(12) United States Patent
Liu et al.

(10) Patent No.: US 7,361,468 B2
(45) Date of Patent: Apr. 22, 2008

(54) METHODS FOR GENOTYPING POLYMORPHISMS IN HUMANS

(75) Inventors: Guoying Liu, Emeryville, CA (US);
Simon Cawley, Oakland, CA (US);
Hajime Matsuzaki, Palo Alto, CA (US); Earl A. Hubbell, Palo Alto, CA (US); Geoffrey Yang, San Jose, CA (US); Teresa A. Webster, Santa Clara, CA (US); Rui Mei, Santa Clara, CA (US); Xiaojun Di, Cupertino, CA (US); Richard Chiles, Castro Valley, CA (US)

(73) Assignee: Affymetrix, Inc., Santa Clara, CA (US)

( * ) Notice: Subject to any disclaimer, the term of this patent is extended or adjusted under 35 U.S.C. 154(b) by 387 days.

(21) Appl. No.: 11/175,859

(22) Filed: Jul. 5, 2005

(65) Prior Publication Data
US 2006/0024715 A1    Feb. 2, 2006

Related U.S. Application Data

(60) Provisional application No. 60/585,352, filed on Jul. 2, 2004.

(51) Int. Cl.
*C12Q 1/68*       (2006.01)
*C07H 21/04*      (2006.01)
*C12M 3/00*       (2006.01)
*C12M 1/34*       (2006.01)

(52) U.S. Cl. ............... 435/6; 435/287.2; 435/91.1; 536/23.1; 536/24.3

(58) Field of Classification Search ............... None
See application file for complete search history.

(56) References Cited

OTHER PUBLICATIONS

GeneChip Human Mapping 10K Array and Assay Kit. 2003, Affymetrix Data Sheet.*

* cited by examiner

*Primary Examiner*—Juliet C. Switzer
(74) *Attorney, Agent, or Firm*—Sandra E. Wells

(57) ABSTRACT

Methods, kits and arrays of nucleic acid probes for genotyping large numbers of human SNPs in parallel are provided. A set of more than 100,000 human SNPs, known to be biallelic in at least two populations is provided. Allele specific perfect match probes and genotyping probe sets are provided for each allele of each biallelic SNP in a set of human SNPs that is useful for genetic analysis within and across populations. Probe sets that include perfect match and mismatch probes are provided. The probe sets are suitable for inclusion in an array. The invention provides the SNP and surrounding sequence and provides the sequences in such a way as to make them available for a variety of analyses including genotyping. As such, the invention relates to diverse fields impacted by the nature of genetics, including biology, medicine, and medical diagnostics.

15 Claims, No Drawings

METHODS FOR GENOTYPING POLYMORPHISMS IN HUMANS

RELATED APPLICATIONS

This application claims the priority of U.S. Provisional Application No. 60/585,352 filed Jul. 2, 2004 the disclosure of which is incorporated herein by reference in its entirety for all purposes.

FIELD OF THE INVENTION

The present invention provides pools of nucleic acid sequences and arrays of nucleic acid sequences that are useful for genotyping polymorphisms in nucleic acid samples derived from humans. The invention relates to diverse fields, including genetics, genomics, biology, population biology, medicine, and medical diagnostics.

REFERENCE TO SEQUENCE LISTING

The Sequence Listing submitted on compact disk is hereby incorporated by reference. The file on the disk is named 3690.1 seqlist.txt, the file is 16.7 MB and the date of creation of the compact discs is Jul. 5, 2005. The machine format for the discs is IBM-PC and the operating system compatibility is MS-WINDOWS 2000.

BACKGROUND

Single nucleotide polymorphisms (SNPs) have emerged as the marker of choice for genome wide association studies and genetic linkage studies. Building SNP maps of the genome will provide the framework for new studies to identify the underlying genetic basis of complex diseases such as cancer, mental illness and diabetes. Identification of the genetic polymorphisms that contribute to susceptibility for common diseases will facilitate the development of diagnostics and therapeutics, see Carlson et al., *Nature* 429:446-452 (2004). Whole-genome association studies may be used to identify polymorphisms with disease associations. These studies require the analysis of much denser panels of markers than are required for linkage analysis in families and benefit from technologies that facilitate the analysis of hundreds of thousands of polymorphisms, see, The International HapMap Consortium, *Nature* 426, 789-796 (2003).

SUMMARY OF THE INVENTION

The invention provides nucleic acid sequences that are complementary to particular regions of the human genome that are known or predicted to contain single nucleotide polymorphisms (SNPs). The invention further provides a collection of SNPs that are useful for performing analysis of the human genome. For example, in one embodiment the invention comprises an array comprising any or more, 1000 or more, 10,000 or more, 100,000 or more, or 1,000,000 or more nucleic acid probes containing 15 or more consecutive nucleotides from the sequences listed in SEQ ID NOS: 1-116,211, or the perfect match, perfect mismatch, antisense match or antisense mismatch thereof. In a preferred embodiment the array comprises 25 nucleotide probes that are 25 consecutive nucleotides from each of the sequences listed in SEQ ID NOS 1-116,211, each probe being a different 25 nucleotide sequence. In a further embodiment, the invention comprises the use of any of the above arrays or fragments disclosed in SEQ ID NOS 1-116,211 to: monitor loss of heterozygosity; identify imprinted genes; genotype polymorphisms; determine allele frequencies in a population, characterize biallelic markers; produce genetic maps; detect linkage disequilibrium, determine allele frequencies, do association studies, analyze genetic variation, to identify markers linked to a phenotype or, compare genotypes between different individuals or populations. In a further embodiment the invention comprises a method of analysis comprising hybridizing one or more pools of nucleic acids to two or more of the fragments disclosed in SEQ ID NOS 1-116,211 and detecting said hybridization. In a further embodiment the invention comprises the use of any one or more of the fragments disclosed in SEQ ID NOS 1-116,211 as a primer for PCR.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods and methods useful for gene expression monitoring and profiling are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,925,525, 6,268,141, 5,856,092, 6,267,152, 6,300, 063, 6,525,185, 6,632,611, 5,858,659, 6,284,460, 6,361,947, 6,368,799, 6,673,579 and 6,333,179. Other methods of nucleic acid amplification, labeling and analysis that may be used in combination with the methods disclosed herein are embodied in U.S. Pat. Nos. 5,871,928, 5,902,723, 6,045, 996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. Modifications to PCR may also be used, for example, the inclusion of Betaine or trimethylglycine, which has been disclosed, for example, in Rees et al. Biochemistry 32:137-144 (1993), and in U.S. Pat. Nos. 6,270,962 and 5,545,539. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) nucleic acid based sequence amplification (NABSA), rolling circle amplification (RCA), multiple displacement amplification (MDA) (U.S. Pat. Nos. 6,124,120 and 6,323,009) and circle-to-circle amplification (C2CA) (Dahl et al. Proc. Natl. Acad. Sci 101:4548-4553 (2004). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 5,409,818, 4,988,617, 6,063,603 and 5,554,517 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. Ser. Nos. 09/916,135, 09/920,491 (U.S. Patent Application Publication 20030096235), 09/910,292 (U.S. Patent Application Publication 20030082543), and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P. N. A. S, 80: 1194 (1983). Methods and apparatus for carrying out repeated and controlled hybridization reactions have been described in U.S. Pat. Nos. 5,871,928, 5,874,219, 6,045,996 and 6,386, 749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. Nos. 10/389, 194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

The whole genome sampling assay (WGSA) is described, for example in Kennedy et al., Nat. Biotech. 21, 1233-1237 (2003), Matsuzaki et al., Gen. Res. 14: 414-425, (2004), and Matsuzaki, et al. Nature Methods 1:109-111 (2004). Algorithms for use with mapping assays are described, for example, in Liu et al., Bioinformatics 19: 2397-2403 (2003) and Di et al. Bioinformatics 21:1958 (2005). Additional methods related to WGSA and arrays useful for WGSA and applications of WGSA are disclosed, for example, in U.S. Patent Application Nos. 60/676,058 filed Apr. 29, 2005, 60/616,273 filed Oct. 5, 2004, 10/912,445, 11/044,831, 10/442,021, 10/650,332 and 10/463,991. Genome wide association studies using mapping assays are described in, for example, Hu et al., *Cancer Res*.; 65(7):2542-6 (2005), Mitra et al., *Cancer Res.*, 64(21):8116-25 (2004), Butcher et al., *Hum Mol Genet.*, 14(10):1315-25 (2005), and Klein et al., *Science*, 308(5720):385-9 (2005). Each of these references is incorporated herein by reference in its entirety for all purposes.

Additionally, the present invention may have preferred embodiments that include methods for providing genetic information over networks such as the Internet as shown in U.S. Ser. Nos. 10/197,621, 10/063,559 (United States Publication Number 20020183936), 10/065,856, 10/065,868, 10/328,818, 10/328,872, 10/423,403, and 60/482,389.

b) Definitions

The term "admixture" refers to the phenomenon of gene flow between populations resulting from migration. Admixture can create linkage disequilibrium (LD).

The term "allele" as used herein is any one of a number of alternative forms a given locus (position) on a chromosome. An allele may be used to indicate one form of a polymorphism, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a bioploymer is a "biomonomer".

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference. When a probe sequence is perfectly complementary to a target it hybridizes to the target without a single mismatch over the entire length of the probe sequence.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. Examples of hybridization conditions include: 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na$^+$], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. In a preferred embodiment 70 ul of labeled DNA is mixed with 190 ul of the following hybridization cocktail: 0.056 M MES, 5.0% DMSO, 2.50× Denhardt's Solution, 5.77 mM EDTA, 0.115 mg/mL Herring Sperm DNA (10 mg/mL), 11.5 μg/mL Human Cot-1, 0.0115% Tween-20, and 2.69 M (3%) TMACL and hybridized to a genotyping array at 16° C.

As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004.

The term "hybridization probes" as used herein are oligonucleotides capable of binding in a base-specific manner to a complementary strand of nucleic acid. Such probes include oligonucleotides, peptide nucleic acids, as described in Nielsen et al., Science 254, 1497-1500 (1991), LNAs, as described in Koshkin et al. Tetrahedron 54:3607-3630, 1998, and U.S. Pat. No. 6,268,490 and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" or sometimes referred to as "allelic association" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., *Nat. Rev. Gen.* 3:299-309, 2002.

The term "lod score" or "LOD" is the log of the odds ratio of the probability of the data occurring under the specific hypothesis relative to the null hypothesis. LOD=log[probability assuming linkage/probability assuming no linkage].

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

C. Interrogation of Selected Human SNPs

SEQ ID NOS 1-116,211, are disclosed. SEQ ID NOS 1-57251 represent SNPs that are found in Hind III fragments of the human genome that are within a selected size range and SEQ ID NOS 57252-116,211 represent SNPs that are present in Xba I fragments of the human genome that are within a selected size range. The sequences provided correspond to one strand of the genomic DNA including the SNP position and 25 bases 5' of the SNP and 24 bases 3' of the SNP. The polymorphic base is at position 26 of the sequences listed in the sequence listing. For example, SEQ ID NO 1 is 5' taatttggaa gacaacaagt tcataYtacc agtctgtctg tcccccagt 3' and the SNP position is represented by Y. The symbols Y, K, M and R are used to represent the SNP position where Y is T or C, K is G or T, M is A or C, and R is G or A. So, for SEQ ID NO 1 the SNP has alleles T and C. Each of SEQ ID Nos. 1-116,211 represents a single SNP from the human genome. SNPs were selected to be included in the list of SNPs and to be interrogated by the mapping array from public databases of SNPs such as dbSNP and from SNPs identified by Perlegen Sciences, Inc. SNPs were selected through a screening and validation process that evaluated accuracy of genotyping calls, rate of genotyping calls, and physical distribution in the genome. The median physical distance between SNPs is 8.5 kb and the average distance between SNPs is 23.6 kb. The average heterozygosity of the SNPs is 0.30.

The SNPs were selected so that the set would broadly cover the human genome, in a preferred embodiment more than 90% of the human genome is within 100 kb of a SNP in the set of SNPs to be genotyped. In another embodiment more than 80% of the genome is within 50 kb of a SNP to be interrogated and more than 40% of the genome is within 10 kb of a SNP to be interrogated. Sets of SNPs that are approximately evenly spaced throughout a genome may be used for linkage and association analysis. In a preferred embodiment the assay allows genotyping of at least 100,000 SNPs using 1 or 2 arrays and costing less than one cent per SNP. More than half of the SNPs in the set have been validated by resequencing at least 50 genomes from 25 individuals. Each allele of each SNP may be interrogated by a single probe sequence or by multiple probe sequences.

The probes of the array are allele specific so if the SNP is either T or C then there is a probe or probe set that is complementary to the T allele and a probe or probe set that is complementary to the C allele and the probe for the T allele is in a different feature of the array than the probe for the C allele. Features are at known or determinable locations.

In a preferred embodiment the array comprises sets of probes to detect the SNPs represented by SEQ ID NOS 1-116,211 or subset of those SNPs. Arrays may detect the genotype of at least 1,000, 5,000, 10,000, 25,000, 50,000 or 100,000 of the SNPs. In one embodiment there are 40 probes for each SNP, comprising 10 quartets of 4 probes. Each quartet consists of a perfect match probe for allele A, a perfect match probe for allele B, a mismatch probe for allele A and a mismatch probe for allele B. The mismatch probe is identical to the perfect match probe with the exception that the central base in the mismatch probe, position 13 in a 25 nucleotide probe, is the complement of the perfect match base. For example, if the perfect match probe has a G at position 13 the mismatch probe has a C at that position. One quartet varies from another in the position of the polymorphic base, for example in one quartet the polymorphic base may be at the central or 0 position of the probe, which is the 13$^{th}$ nucleotide from the 5' end of a 25 nucleotide probe. In the other quartets the polymorphic base may be shifted 5' or 3' of the 0 position. Thus, each 50 nucleotide sequence in the sequence listing represents at least 40 different probes that contain at least 15 contiguous nucleotides of a sequence from the sequence listing. An example of a genotyping probe set of a preferred embodiment for a SNP, SNP 611, is shown in Table 1.

TABLE 1

| SEQ ID NO | PM/ MM, A/G | Position | Probe Sequence | Strand |
|---|---|---|---|---|
| 116,212 | PM A | -4 | TCATTTAACATTTGTGTTAACAAAA | 0 |
| 116,213 | MM A | -4 | TCATTTAACATTAGTGTTAACAAAA | 0 |
| 116,214 | PM A | -2 | ATTTAACATTTGTGTTAACAAAAAC | 0 |
| 116,215 | MM A | -2 | ATTTAACATTTGAGTTAACAAAAAC | 0 |
| 116,216 | PM A | -1 | TTTAACATTTGTGTTAACAAAAACT | 0 |
| 116,217 | MM A | -1 | TTTAACATTTGTCTTAACAAAAACT | 0 |
| 116,218 | PM A | 0 | TTAACATTTGTGTTAACAAAAACTC | 0 |
| 116,219 | MM A | 0 | TTAACATTTGTGATAACAAAAACTC | 0 |
| 116,220 | PM A | 1 | TAACATTTGTGTTAACAAAAACTCC | 0 |
| 116,221 | MM A | 1 | TAACATTTGTGTAAACAAAAACTCC | 0 |
| 116,222 | PM A | 4 | CATTTGTGTTAACAAAAACTCCTCC | 0 |

TABLE 1-continued

| SEQ ID NO | PM/ MM, A/G | Position | Probe Sequence | Strand |
|---|---|---|---|---|
| 116,223 | MM A | 4 | CATTTGTGTTAAGAAAAACTCCTCC | 0 |
| 116,224 | PM G | -4 | TCATTTAACATTTGTGCTAACAAAA | 0 |
| 116,225 | MM G | -4 | TCATTTAACATTAGTGCTAACAAAA | 0 |
| 116,226 | PM G | -2 | ATTTAACATTTGTGCTAACAAAAAC | 0 |
| 116,227 | MM G | -2 | ATTTAACATTTGAGCTAACAAAAAC | 0 |
| 116,228 | PM G | -1 | TTTAACATTTGTGCTAACAAAAACT | 0 |
| 116,229 | MM G | -1 | TTTAACATTTGTCCTAACAAAAACT | 0 |
| 116,230 | PM G | 0 | TTAACATTTGTGCTAACAAAAACTC | 0 |
| 116,231 | MM G | 0 | TTAACATTTGTGGTAACAAAAACTC | 0 |
| 116,232 | PM G | 1 | TAACATTTGTGCTAACAAAAACTCC | 0 |
| 116,233 | MM G | 1 | TAACATTTGTGCAAACAAAAACTCC | 0 |
| 116,234 | PM G | 4 | CATTTGTGCTAACAAAAACTCCTCC | 0 |
| 116,235 | MM G | 4 | CATTTGTGCTAAGAAAAACTCCTCC | 0 |
| 116,236 | PM A | -4 | TTTTGTTAACACAAATGTTAAATGA | 1 |
| 116,237 | MM A | -4 | TTTTGTTAACACTAATGTTAAATGA | 1 |
| 116,238 | PM A | -2 | GTTTTGTTAACACAAATGTTAAAT | 1 |
| 116,239 | MM A | -2 | GTTTTGTTAACTCAAATGTTAAAT | 1 |
| 116,240 | PM A | -1 | AGTTTTGTTAACACAAATGTTAAA | 1 |
| 116,241 | MM A | -1 | AGTTTTGTTAAGACAAATGTTAAA | 1 |
| 116,242 | PM A | 0 | GAGTTTTGTTAACACAAATGTTAA | 1 |
| 116,243 | MM A | 0 | GAGTTTTGTTATCACAAATGTTAA | 1 |
| 116,244 | PM G | -4 | TTTTGTTAGCACAAATGTTAAATGA | 1 |
| 116,245 | MM G | -4 | TTTTGTTAGCACTAATGTTAAATGA | 1 |
| 116,246 | PM G | -2 | GTTTTGTTAGCACAAATGTTAAAT | 1 |
| 116,247 | MM G | -2 | GTTTTGTTAGCTCAAATGTTAAAT | 1 |
| 116,248 | PM G | -1 | AGTTTTGTTAGCACAAATGTTAAA | 1 |
| 116,249 | MM G | -1 | AGTTTTGTTAGGACAAATGTTAAA | 1 |
| 116,250 | PM G | 0 | GAGTTTTGTTAGCACAAATGTTAA | 1 |
| 116,251 | MM G | 0 | GAGTTTTGTTACCACAAATGTTAA | 1 |

The exemplary probe set shown in Table 1 has 40 probes. The two strands of the DNA are indicated by 0 or 1. There are 10 sets of 4 probes. Each set has 2 perfect match probes, 1 for each allele and 2 mismatch probes. In this set there are 24 probes, (6 probe sets of 4 probes), for the 0 strand and 16 probes, (4 probe sets of 4 probes), for the 1 strand. The probe sets for the 0 strand correspond to having the SNP allele at positions -4, -2, -1, 0, 1 and 4 of the probe and the probe sets for the 1 strand correspond to the SNP allele at positions -4, -2, -1 and 0 of the probe (where 0 is the central position of the probe). As shown by this example there can be an unequal number of probe sets for the 0 and 1 strand. PM A indicates perfect match probes for allele A and PM G indicates perfect match probes for allele G. Mismatch probes for allele A and G are indicated by MM A and MM G, respectively.

In a preferred embodiment the optimal 10 quartets are selected for each SNP. This may be 5 quartets for each of the two strands or an unequal number of quartets from each strand, for example, 6 from one strand and 4 from the other as in the example in Table 1. There may be 7 and 3, 8 and 2, 9 and 1 or 10 and 0. The quartets may vary in the position of the SNP base. For example, the 5 quartets may be 0, +2, +4, −3, and −4 on one strand and 0, +1, +3, −2, and −4 on the opposite strand. In some embodiments the quartets for one strand correspond to the quartets from the other strand so that the probes from one quartet are the complements of the probes from the corresponding quartet.

In the example probe set provided in Table 1, SEQ ID No. 116,212 has a T at position 13 and a T at position 17 and is the perfect match (PM) A probe. SEQ ID No. 116,213 has an A at position 13 and a T at position 17 and is the mismatch (MM) A probe. Position 13 is the position of the mismatch base in the MM A probe and position 17 is the position of the allele specific SNP base. The SNP position is shifted to the −4 position relative to the 0 strand. The −4 G allele probes are SEQ ID Nos. 116,224 and 116,225 and they have a C at position 17. The −4 probes for the A allele for the 1 strand, the opposite strand, are SEQ ID Nos. 116,236 and 116,237. The mismatch is at position 13 and the SNP allele is at position 9.

Accordingly, for each nucleic acid sequence listed in SEQ ID NOS 1-116,211, this disclosure includes a probe comprising any contiguous length of from 15 to 50 nucleotides from a sequence in the list or the complement of a sequence in the list. The oligonucleotides may also comprise any contiguous length from 15 to 50 nucleotides from a sequence in the list or the complement of a sequence in the list including a single base mismatch. The position of the mismatch is preferably located at the central position of the probe, for example, for a probe of 25 nucleotides, the mismatch position would be position 13. In another embodiment the mismatch position may be located anywhere in the nucleic acid sequence and may comprise one base, or in some embodiments there may be 2, 3, 4 or 5 mismatches. Generally, the sequences correspond to SNPs each represented by a single sequence from SEQ ID Nos. 1-116,211, which include the SNP position and sequences surrounding the SNP. The SNPs are preferably biallelic but may be triallelic and the probes in a preferred embodiment are used to distinguish between different alleles of a SNP. Allele frequencies vary between populations so a SNP that is biallelic in one population may not be polymorphic in another population or may be represented by different alleles or different allele frequencies.

The present invention includes: the sequences listed in SEQ ID NOS 1-116,211 and the complement of these sequences. In a preferred aspect an array including a genotyping probe set of at least 20 probes for at least 10,000 SNPs, designed from sequences in the sequence listing according to the example in Table 1, is disclosed. Also contemplated are mismatch probes incorporating at least 15 bases from SEQ ID NOS 1-116,211, longer nucleotide sequences which include at least one of the nucleic acid sequences listed in SEQ ID NOS 1-116,211 and the complement of these sequences and sub-sequences greater than 15 nucleotides in length of the target nucleic acid sequences listed in SEQ ID NOS 1-116,211 and the complement of these sequences. Also disclosed are oligonucleotides that comprise 15 to 50 contiguous nucleotides from one of the sequences in SEQ ID No. 1-116,211 or the complement of SEQ ID No. 1-116,211 and additional sequence 5' or 3'. For example, oligonucleotides or probes may comprise one or more tag sequences, universal priming sequence, or restriction enzyme recognition sequences upstream or downstream (5' or 3') of a region comprising 15 to 50 contiguous nucleotides of SEQ ID No. 1-116,211. The oligonucleotides may be attached to a solid support, for example, each different sequence may be attached to one or more beads. In one embodiment an oligonucleotide that is complementary to each allele of each of the SNPs represented by SEQ ID No. 1-116,211 is attached to an array in a determinable location that is different from a plurality of other different sequence oligonucleotides. The oligonucleotides may be extended in an allele specific manner and extension detected. For example, extension may be with labeled nucleotides and may also be allele specific. Differently tagged oligos may be used for each allele of each SNP. See, for example, U.S. Pat. Nos. 6,709,816, 6,287,778, and 6,638,719. Tags, tag probes, arrays of tag probes, methods of using tags, and methods of selecting sets of tags are disclosed, for example, in U.S. Pat. Nos. 6,458,530 and 6,656,412 and in U.S. patent application Ser. No. 09/827,383.

The nucleic acid sequences listed in SEQ ID NOS 1-116,211 correspond to regions of the human genome containing SNPs. Information about the SNPs represented by each of the sequences in the sequence listing can be obtained from public databases. Each SNP has a reference SNP ID or "rs" ID that identifies a SNP in the NCBI (National Center for Biotechnology Information) SNP database (dbSNP). A reference SNP ID, or 'rs' ID is an identification tag assigned by NCBI to SNPs that appear to be unique in the database. The rs ID number, or tag, is assigned at submission. For example, 1000018A, refers to the A allele of a SNP at position 62126003 of chromosome 2. The observed alleles are A and T. A search of the dbSNP database for rs1000018 provides available information about the SNP. For each of the SNP IDs represented in the sequence listing the corresponding entry in dbSNP is incorporated by reference (Build 116, Aug. 2, 2003).

SNPs were selected from the publicly available database of human SNPs. The selected SNPs are from the group of SNPs that are present on XbaI or HindIII fragments of 250 to 2000 base pairs. A computer system was used to predict fragments that would result when the human genome is digested with XbaI or HindIII. Those fragments in the selected size range were selected for further analysis. Of those fragments those that carried a SNP were selected as potential target sequences. SNPs were selected from these potential target sequences and the selected SNPs are represented by SEQ ID NOS 1-116,211. In some embodiments the present invention provides one or more pools of unique nucleotide sequences complementary to SNPs and sequence surrounding SNPs which alone, or in combinations of 2 or more, 10 or more, 100 or more, 1,000 or more, 10,000 or more or 100,000 or more can be used for a variety of applications.

In one embodiment, the present invention provides for a pool of unique nucleotide sequences which are complementary to human SNPs and sequence surrounding SNPs formed into a high density array of probes suitable for array based massive parallel gene expression. Array based methods for SNP analysis and genotyping are disclosed and discussed in detail in U.S. Pat. Nos. 6,361,947 and 6,368,799 which are incorporated herein by reference for all purposes. Generally those methods of SNP analysis involve: (1) providing a pool of target nucleic acids comprising one or more target sequence(s), (2) amplifying a collection of target sequences, (3) hybridizing the amplified nucleic acid sample to a high density array of probes, and (4) detecting the hybridized nucleic acids and determining the presence or absence of one or more alleles for one or more SNPs.

The development of Very Large Scale Immobilized Polymer Synthesis or VLSIPS™ technology has provided methods for making very large arrays of nucleic acid probes in very small arrays. See U.S. Pat. No. 5,143,854 and PCT Nos. WO 90/15070 and 92/10092, and Fodor et al., *Science*, 251:767-77 (1991), each of which is incorporated herein by reference. U.S. Pat. Nos. 5,800,992 and 6,040,138 describe methods for making arrays of nucleic acid probes that can be used to detect the presence of a nucleic acid containing a specific nucleotide sequence. Methods of forming high-density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling. See also US Pub. Nos. 20030003490, 20020187515, and 20020177141.

In one embodiment probes are present on the array so that each SNP is represented by a collection of probes. The array may comprise between 4 and 80 probes for each SNP. In one embodiment the collection comprises, between 20 and 40 probes for each SNP. In another embodiment the array comprises about 40 to about 56 probes for each SNP. In a preferred embodiment the collection comprises about 40 probes for each SNP, 20 for each allele. In one embodiment the probes may be present in sets of 8 probes that correspond to a PM probe for each of two alleles, a MM probe for each of 2 alleles, and the corresponding probes for the opposite strand. In another embodiment the probes may be present in sets of 4 probes that correspond to a PM probe for each of two alleles and a MM probe for each of 2 alleles, all complementary to the same strand. The polymorphic position may be the central position of the probe region, for example, the probe region may be 25 nucleotides and the polymorphic allele may be in the middle with 12 nucleotides on either side. In other probe sets the polymorphic position may be offset from the center. For example, the polymorphic position may be from 1 to 7 bases from the central position on either the 5' or 3' side of the probe. The interrogation position, which is changed in the mismatch probes, may remain at the center position. In one embodiment there are 56 probes for each SNP: the 8 probes corresponding to the polymorphic position at the center or 0 position and 8 probes for the polymorphic position at each of the following positions: −4, −2, −1, +1, +3 and +4 relative to the central or 0 position. In another embodiment 40 probes are used, 8 for the 0 position and 8 for each of 4 additional positions selected from: −4, −2, −1, +1, +3 and +4 relative to the central or 0 position. The probes sets used may vary depending on the SNP, for example, for one SNP the probes may be −4, −2, 0, +1 and +4 and for another SNP they may be −2, −1, 0, +1 and +4. Empirical data may be used to choose which probe sets to use on an array. In another embodiment 24 or 32 probes may be used for one or more SNPs.

In many embodiments pairs are present in perfect match and mismatch pairs, one probe in each pair being a perfect match to the target sequence and the other probe being identical to the perfect match probe except that the central base is a homo-mismatch. Mismatch probes provide a control for non-specific binding or cross-hybridization to a nucleic acid in the sample other than the target to which the probe is directed. Thus, mismatch probes indicate whether hybridization is or is not specific. For example, if the target is present, the perfect match probes should be consistently brighter than the mismatch probes because fluorescence intensity, or brightness, corresponds to binding affinity. (See e.g., U.S. Pat. No. 5,324,633, which is incorporated herein for all purposes.) Finally, the difference in intensity between the perfect match and the mismatch probe (I(PM)−I(MM)) provides a good measure of the concentration of the hybridized material. See PCT No. WO 98/11223, which is incorporated herein by reference for all purposes.

In another embodiment, the current invention provides a pool of sequences that may be used as probes. Methods for making probes are well known. See e.g., MOLECULAR CLONING A LABORATORY MANUAL, Sambrook and Russell Eds., CSLH Press, ($3^{rd}$ ed. 2001), which is hereby incorporated in its entirety by reference for all purposes. Sambrook describes a number of uses for nucleic acid probes of defined sequence. Some of the uses described by Sambrook include: (1) screening cDNA or genomic DNA libraries, or subclones derived from them, for additional clones containing segments of DNA that have been isolated and previously sequenced; (2) identifying or detect the sequences of specific genes; (3) detecting specific mutations in genes of known sequence; to detect specific mutations generated by site-directed mutagenesis of cloned genes; (4) and mapping the 5' termini of mRNA molecules by primer extensions. Sambrook describes other uses for probes throughout. See also Alberts et al., MOLECULAR BIOLOGY OF THE CELL ($3^{rd}$ ed. 1994) at 307 and Lodish et al., MOLECULAR CELL BIOLOGY, ($4^{th}$ ed. 2000) at 285-286, each of which is hereby incorporated by reference in its entirety for all purposes, for a brief discussion of the use of nucleic acid probes in in situ hybridization. Other uses for probes derived from the sequences disclosed in this invention will be readily apparent to those of skill in the art. See e.g., Lodish et al., MOLECULAR CELL BIOLOGY, ($3^{rd}$ ed. 1995) at 229-233, incorporated above, for a description of the construction of genomic libraries.

In another embodiment, the current invention may be combined with known methods to genotype polymorphism in a wide variety of contexts. For example, the methods may be used to do association studies, identify candidate genes associated with a phenotype, genotype SNPs in clinical populations, or correlate genotype information to clinical phenotypes. The SNPs of Table 1 have been selected based on a number of criteria that make them suitable for complex genetic analysis, for example, linkage analysis and association studies. The SNPs in the set of SNPs represented by the sequence listing are spaced throughout the genome at an average distance of 210 Kb from one another and they are known to be polymorphic in multiple populations. The panel of SNPs or a subset of these SNPs may be genotyped by any method available. See, Color Atlas of Genetics ($2^{nd}$ ed), Ed. Passarge (2001) Thieme, NY, N.Y., which is incorporated by reference.

For a discussion of genotyping analysis methods see, for example, Elena and Lenski Nature Reviews, Genetics 4:457-469 (2003), Twyman and Primrose, Pharmacogenomics 4:67-79 (2003), Hirschhorn et al. Genetics in Medicine 4:45-61 (2002) and Glazier et al. *Science* 298:2345-2349 (2002) each of which is incorporated herein by references for all purposes. For a discussion of high throughput genotyping approaches see, for example, Jenkins and Gibson, *Comp Funct Genom* 2002; 3:57-66 which is incorporated herein by reference. For a review of methods of haplotype analysis in population genetics and association studies see, for example, Zhao et al. Pharmacogenomics 4:171-178 (2003), which is incorporated herein by reference.

In preferred embodiments the SNPs are genotyped by amplification of the sample using the whole genome sampling assay, (WGSA), hybridization to a mapping array as disclosed herein and analysis of the hybridization pattern using software that provides genotyping calls. WGSA is described, for example in Kennedy et al., Nat. Biotech. 21, 1233-1237 (2003), Matsuzaki et al., Gen. Res. 14: 414-425, (2004), and Matsuzaki, et al. Nature Methods 1: 109-111 (2004). Algorithms for use with mapping assays are described, for example, in Liu et al., Bioinformatics 19: 2397-2403 (2003) and Di et al. Bioinformatics 21:1958 (2005). Additional methods related to WGSA and arrays useful for WGSA and applications of WGSA are disclosed, for example, in U.S. Patent Application Nos. 60/676,058 filed Apr. 29, 2005, 60/616,273 filed Oct. 5, 2004, 10/912, 445, 11/044,831, 10/442,021, 10/650,332 and 10/463,991. Genome wide association studies using mapping assays are described in, for example, Hu et al., Cancer Res.;65(7): 2542-6 (2005), Mitra et al., Cancer Res., 64(21):8116-25 (2004), Butcher et al., Hum Mol Genet., 14(10):1315-25 (2005), and Klein et al., Science, 308(5720):385-9 (2005). Each of these references is incorporated herein by reference in its entirety for all purposes.

One skilled in the art will appreciate that a wide range of applications will be available using 2 or more, 10 or more, 100 or more, 1000 or more, 10,000 or more, 100,000 or more, or more of the SEQ ID NOS 1-116,211 sequences as probes for polymorphism detection and analysis. The combination of the DNA array technology and the Human SNP specific probes in this disclosure is a powerful tool for genotyping and mapping disease loci.

In many embodiments the target sequences are a subset that is representative of a larger set. For example, the target sequences may be 1,000, 5,000, 10,000 or 100,000 to 10,000, 20,000, 100,000, 1,500,000 or 3,000,000 SNPs that may be representative of a larger population of SNPs present in a population of individuals. The target sequences may be dispersed throughout a genome, including for example, sequences from each chromosome, or each arm of each chromosome. Target sequences may be representative of haplotypes or particular phenotypes or collections of phenotypes. For a description of haplotypes see, for example, Gabriel et al., Science, 296:2225-9 (2002), Daly et al. Nat Genet., 29:229-32 (2001) and Rioux et al., Nat Genet., 29:223-8 (2001), each of which is incorporated herein by reference in its entirety.

In another embodiment, the present invention may be used for cross-species comparisons. One skilled in the art will appreciate that it is often useful to determine whether a SNP present in one species, for example human, is present in a conserved format in another species, including, without limitation, gorilla, chimp, mouse, rat, or chicken. See e.g. Andersson et al., Mamm. Genome, 7(10):717-734 (1996), which is hereby incorporated by reference for all purposes, which describes the utility of cross-species comparisons. The use of 2 or more, 10 or more, 100 or more, 1000 or more, 10,000 or more, 100,000 or more of the sequences disclosed in this invention in an array can be used to determine whether any sequence from one or more of the human SNPs represented by the sequences disclosed in this invention is conserved in another species by, for example, hybridizing genomic nucleic acid samples from another species to an array comprised of the sequences and probe sets disclosed in this invention.

In a preferred embodiment, the hybridized nucleic acids are detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. Thus, for example, polymerase chain reaction (PCR) with labeled primers or labeled nucleotides will provide a labeled amplification product. In another embodiment, transcription amplification using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore). In another embodiment label is added to the end of fragments using terminal deoxytransferase (TdT).

Detectable labels suitable for use in the present invention include any composition detectable by spectroscopic, photochemical, biochemical, immunochemical, electrical, optical or chemical means. Useful labels in the present invention include, but are not limited to: biotin for staining with labeled streptavidin conjugate; anti-biotin antibodies, magnetic beads (e.g., Dynabeads™); fluorescent dyes (e.g., fluorescein, texas red, rhodamine, green fluorescent protein, and the like); radiolabels (e.g., $^3$H, $^{125}$I, $^{35}$S, $^{14}$C, or $^{32}$P); phosphorescent labels; enzymes (e.g., horse radish peroxidase, alkaline phosphatase and others commonly used in an ELISA); and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target nucleic acid(s) prior to, or after the hybridization. So called "direct labels" are detectable labels that are directly attached to or incorporated into the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids. See Tijssen, LABORATORY TECHNIQUES IN BIOCHEMISTRY AND MOLECULAR BIOLOGY, VOL. 24: HYBRIDIZATION WITH NUCLEIC ACID PROBES (1993) which is hereby incorporated by reference in its entirety for all purposes.

D. Methods of Use

The methods of the presently claimed invention can be used for a wide variety of applications including, for example, linkage and association studies, identification of candidate gene regions, genotyping clinical populations, correlation of genotype information to phenotype information, loss of heterozygosity analysis, and identification of the source of an organism or sample, or the population from which an organism or sample originates. Any analysis of genomic DNA may be benefited by a reproducible method of polymorphism analysis. Furthermore, the probes, sequences, arrays and collections of SNPs of the presently claimed invention are particularly well suited for study and characterization of extremely large regions of genomic DNA in individual samples and in populations.

In a preferred embodiment, the methods of the presently claimed invention are used to genotype individuals, populations or samples. For example, any of the procedures described above, alone or in combination, could be used to interrogate SNPs present in Table 1. The disclosed arrays could be used in conjunction with methods of reducing the complexity of a sample in a reproducible and predictable manner. For example, complexity reduction methods may be designed to amplify a collection of target sequences that correspond to fragments containing SNPs from Table 1. Arrays may be designed and manufactured on a large scale basis to interrogate those fragments with probes comprising sequences from SEQ ID NOS 1-116,211. Thereafter, a sample from one or more individuals would be obtained and prepared using the same techniques which were used to prepare the selection probes or to design the array. Each sample can then be hybridized to an array and the hybridization pattern can be analyzed to determine the genotype of each individual or a population of individuals. Methods of use for polymorphisms and SNP discovery can be found in, for example, U.S. Pat. No. 6,361,947 which is herein incorporated by reference in its entirety for all purposes.

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000-2,000 bases when two human chromosomes are compared, resulting in an estimated 3,000,000 SNPs in the human genome. (See, The International SNP Map Working Group, Science 409: 928-933 (2001) incorporated herein by reference in its entirety for all purposes.) Human diversity is limited not only by the number of SNPs occurring in the genome but further by the observation that specific combinations of alleles are found at closely linked sites, generating haplotypes. For a description of haplotypes see, for example, Gabriel et al., Science, 296:2225-9 (2002), Daly et al. Nat Genet., 29:229-32 (2001) and Rioux et al., Nat Genet., 29:223-8 (2001), each of which is incorporated herein by reference in its entirety.

Correlation of individual polymorphisms or groups of polymorphisms with phenotypic characteristics is a valuable tool in the effort to identify DNA variation that contributes to population variation in phenotypic traits. Phenotypic traits include, for example, physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic. Large scale association studies using large groups of SNPs provides additional tools for disease association studies.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531-537 (2001) hereby incorporated by reference in its entirety for all purposes.) The arrays may be used for any application that uses genotype information, for examples, applications such as pharmacogenomics, translational medicine, paternity analyis, linkage, association, allele frequency determination, relatedness determination, forensics and genetic mapping.

EXAMPLE

The following example serves to illustrate the type of experiment that could be conducted using the invention.

The GeneChip® Human Mapping 100K set comprises two arrays, each with greater that 50,000 SNPs interrogated per array. The first array comprises probe sets to SNPs on human genome XbaI fragments and the second array comprises probe sets for SNPs on human genome HindIII fragments. Researchers can use one of the arrays to genotype more than 50,000 SNPs in a single experiment or use both arrays to genotype more than 100,000 SNPs. The arrays can be used alone or in combination. The arrays may be used for linkage and association studies. Detailed methods for sample preparation, array hybridization and analysis are disclosed, for example, in U.S. provisional application No. 60/556,753 and U.S. patent application Ser. No. 10/681,773. In general genomic DNA is amplified, labeled and hybridized to arrays. Total genomic DNA (250 ng) is digested with a restriction enzyme (XbaI or HindIII) and ligated to adapters that recognize the cohesive four basepair overhangs. All fragments resulting from digestions, regardless of size, are substrates for adapter ligation. A generic primer that recognizes the adapter sequence is used to amplify adapter ligated DNA fragments. PCR conditions optimized to preferentially amplify fragments in the 250 to 2000 bp size range are used for amplification. The amplified DNA is fragmented, labeled and hybridized to the Mapping 100K set. See, the GeneChip Mapping 100K assay manual for additional information.

Polymorphism Detection by Hybridization to High Density Oligonucleotide Arrays

Arrays containing the desired number of probes can be synthesized using the method described in U.S. Pat. No. 5,143,854, incorporated by reference above. Nucleic acid may be amplified so that a collection of target sequences is preferentially amplified. The amplified fragments may be fragmented and end labeled with terminal deoxytransferase and biotin labeled nucleotides. Hybridizations are carried out in a flow cell that contains the two-dimensional DNA probe arrays. Following a brief washing step to remove unhybridized RNA, the arrays are scanned using a scanning confocal microscope.

250 ng Genomic DNA was digested with XbaI or HindIII by mixing 5 µl 50 ng/µl human genomic DNA (Coriell Cell Repositories) with 10.5 µl H$_2$0 (Accugene), 2 µl 10×RE buffer (NEB, Beverly, Mass.), 2 µl 10×BSA (NEB, Beverly, Mass.), and 0.5 µl XbaI or HindIII (NEB, Beverly, Mass.). The reaction was incubated at 30° C. for 2 hours, then the enzyme was inactivated by incubation at 70° C. for 20 min and then to 4° C. The reaction may be stored at −20° C.

For ligation of the adapters the digested DNA was then mixed with 1.25 µl 5 uM adapter in TE pH 8.0, 2.5 µl T4 DNA ligation buffer and 1.25 µl T4 DNA Ligase (NEB, Beverly, Mass.) which is added last. The reaction was incubated at 16° C. for 2 hours then at 70° C. for 20 min and then to 4° C. The 25 µl ligation mixture is then diluted with 75 µl H$_2$0 and may be stored at −20° C.

For PCR 10 µl of the diluted ligated DNA is mixed with 10 µl PCR buffer II (Perkin Elmer, Boston, Mass.), 10 µl 2.5 mM dNTP (PanVera Takara, Madison, Wis.), 10 µl 25 mM MgCl$_2$, 7.5 µl 10 µM primer (for a final concentration of 0.75 µM), 2 µl 5U/µl Taq Gold (Perkin Elmer, Boston, Mass.) and 50.5 µl H$_2$0. For each array four 100 µl reactions were prepared. Amplification was done using the following program: 95° C. for 3 min; 35 cycles of 95° C. for 20 sec, 59° C. for 15 sec and 72° C. for 15 sec; and a final incubation at 72° C. for 7 min. The reactions were then held at 4° C. The lid heating option was selected.

The PCR reactions were then purified by mixing the 100 µl PCR reaction with 500 µl PB or PM buffer into Qiagen columns (Valencia, Calif.) and the column was centrifuged at 13,000 rpm for 1 min. Flow through was discarded and 750 µl PE buffer with ethanol was added into the column to wash the sample and the column was spun at 13,000 rpm for 1 min. The flow through was discarded and the column was spun at 13,000 rpm for another 1 min. The flow through was discarded and the column was placed in a new collection tube. For 2 of the 4 samples 30 µl of EB elution buffer pH 8.5 was added to the center of the QIAquick membrane to elute the sample and the columns were allowed to stand at room temperature for 5 min and then centrifuged at 13,000 for 1 min. The elution buffer from the first 2 samples was then used to elute the other 2 samples and the eluates were combined. The DNA was quantified and diluted so that 48 µl contains 20 µg DNA.

The DNA was fragmented by mixing 48 µl DNA (20 µg), 5 µl RE Buffer 4, and 2 µl 0.09 U/µl DNase in a total volume of 55 µl. The reaction was incubated at 37° C. for 30 min then 95° C. for 15 min and then held at 4° C.

Fragments were labeled using GeneChip DNA labeling reagent and TdT as described in the 100K manual.

Hybridization mix is 12 µl 1.22 M MES, 13 µl DMSO, 13 µl 50× Denharts, 3 µl 0.5M EDTA, 3 µl 10 mg/ml herring sperm DNA, 3 µl 10 nM oligo B2, 3 µl 1 mg/ml Human Cot-1, 3 µl 1% Tween-20, and 140 µl 5M TMACL. 70 µl labeled DNA was mixed with 190 µl hybridization mix. The mixture was incubated at 95° C. for 10 min, spun briefly and held at 47.5° C. 200 µl of the denatured mixture was hybridized to an array at 47.5° C. for 16 to 18 hours at 60 rpm. The sample was hybridized to either the XbaI array or the HindIII array. Each probe is present in a spatially addressable location.

Staining mix was 990 µl H$_2$0, 450 µl 20× SSPE, 15 µl Tween-20, 30 µl 50% Denharts. For the first stain mix 495 µl staining mix with 5 µl 1 mg/ml streptavidin (Pierce Scientific, Rockford, Ill.), for the second stain mix 495 µl staining mix with 5 µl 0.5 mg/ml biotinylated anti-streptavidin antibody (Vector Labs, Burlingame, Calif.) and for the third stain mix 495 µl staining mix with 5 µl 1 mg/ml streptavidin, R-phycoerythrin conjugate (Molecular Probes, Eugene, Oreg.). Wash and stain under standard conditions.

Hybridized samples were analyzed with a computer system to determine which alleles were present for a particular SNP.

CONCLUSION

The inventions herein provide a pool of unique nucleic acid sequences, which may be used to genotype a collection of Human SNPs. These sequences can be used for a variety of types of analyses.

The above description is illustrative and not restrictive. Many variations of the invention will become apparent to those of skill in the art upon review of this disclosure. The scope of the invention should, therefore, be determined not with reference to the above description, but instead be determined with reference to the appended claims along with their full scope of equivalents.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07361468B2). An electronic copy of the "Sequence Listing" will also be available from the USPTO upon request and payment of the fee set forth in 37 CFR 1.19(b)(3).

What is claimed is:

1. An array of oligonucleotides, the array consisting of: a plurality of different allele specific perfect match probes attached to a solid support, wherein each allele specific perfect match probe consists of 20 to 50 contiguous nucleotides from a different sequence listed in SEQ ID Nos. 1-116,211 and wherein the plurality of different allele specific perfect match probes consists of at least one probe consisting of between 20 and 50 contiguous nucleotides from each of SEQ ID NOs. 1-116,211; wherein each of the allele specific perfect match probes overlaps with nucleotide 26 of the sequence given in the respective SEQ ID NO, and each probe is perfectly complementary to one of the two possible alleles, and wherein each different allele specific perfect match probe is attached to a solid support in a known or determinable location of the array, wherein the two possible alleles are nucleotides allowed by the degenerate symbol at position 26 of the sequence given in the respective SEQ ID NO.

2. The array of claim 1 wherein the plurality of different allele specific perfect match probes consists of a first allele specific perfect match probe for the first allele of each SNP represented by SEQ ID Nos. 1-116,211 and a second allele specific perfect match probe for the second allele of each SNP represented by SEQ ID Nos. 1-116,211, wherein the SNP is represented by the degenerate nucleotide symbol at position 26 of the listed sequences, and the two alleles are nucleotides allowed by the degenerate symbol.

3. The array of claim 1 wherein each of the allele specific perfect match probes for a selected allele of a selected SNP varies from every other allele specific perfect match probe for that allele of that SNP in the position of the polymorphic base relative to the center of the probe.

4. The array of claim 3 wherein the polymorphic base in a probe is in a position selected from −7, −6, −5, −4, −3, −2, −1, 0, 1, 2, 3, 4, 5, 6, or 7 relative to the center, where 0 is the central position of the probe.

5. The array of claim 4 wherein the probes are 25 bases in length.

6. The array of claim 1 wherein each allele specific perfect match probe is attached to a different bead.

7. A method of genotyping single nucleotide polymorphisms in parallel comprising:
obtaining a nucleic acid sample;
amplifying fragments of DNA in the nucleic acid sample;
hybridizing the amplified sample to the array of claim 1
analyzing the resulting hybridization pattern; and
determining the genotype of the sample for each of the single nucleotide polymorphisms.

8. The method of claim 7 wherein the solid support is a plurality of beads wherein each allele specific perfect match probe is attached to a different bead.

9. The method of claim 7 wherein the step of amplifying fragments of DNA in the nucleic acid sample comprises fragmenting the sample with at least one restriction enzyme, ligating an adapter to at least some of the fragments to generate adapter ligated fragments, and amplifying at least some of the adapter ligated fragments by polymerase chain reaction using a primer to the adapter.

10. The method of claim 9 wherein the at least one restriction enzyme is selected from the group consisting of XbaI and HindIII.

11. The method of claim 7 wherein the step of amplifying fragments of DNA in the nucleic acid sample comprises:
(a) fragmenting a first aliquot of the sample with a first restriction enzyme to generate a first fragmented aliquot;
(b) fragmenting a second aliquot of the sample with a second restriction enzyme to generate a second fragmented aliquot;
(c) ligating a first adapter to at least some of the fragments in the first fragmented aliquot;
(d) ligating a second adapter to at least some of the fragments in the second fragmented aliquot;
(e) amplifying at least some of the fragments from (c); and,
(f) amplifying at least some of the fragments from (d); and wherein the product of step (e) is hybridized to a first solid support and the product of step (f) is hybridized to a second solid support.

12. The method of claim 11 wherein the first restriction enzyme is XbaI, the second restriction enzyme is HindIII and the first primer and the second primer have the same sequence.

13. The method of claim 7 wherein the steps of analyzing the resulting hybridization pattern; and determining the genotype of the sample for each of the single nucleotide polymorphisms are performed by a computer.

14. The method of claim 7 wherein the nucleic acid sample is from a human.

15. The method of claim 7 wherein the nucleic acid sample is from a non-human primate.

* * * * *